US005759516A

United States Patent [19]

Zamora et al.

[11] Patent Number: 5,759,516
[45] Date of Patent: *Jun. 2, 1998

[54] PEPTIDE-METAL ION PHARMACEUTICAL PREPARATION

[75] Inventors: Paul O. Zamora; Buck A. Rhodes. both of Albuquerque, N. Mex.

[73] Assignee: Rhomed Incorporated, Albuquerque, N. Mex.

[*] Notice: The term of this patent shall not extend beyond the expiration date of Pat. No. 5,556,609.

[21] Appl. No.: 454,949

[22] Filed: May 31, 1995

Related U.S. Application Data

[60] Division of Ser. No. 840,077, Feb. 20, 1992, Pat. No. 5,443,816, which is a continuation-in-part of Ser. No. 565, 275, Aug. 8, 1990, Pat. No. 5,102,990.

[51] Int. Cl.$^6$ .................. A61K 51/00; A61M 36/14
[52] U.S. Cl. .................. 424/1.69; 424/1.11; 424/1.65; 530/300; 534/10
[58] Field of Search .................. 424/1.65, 1.69, 424/9.1, 1.11; 530/300, 326, 327, 328, 329, 330; 534/10, 14

[56] References Cited

U.S. PATENT DOCUMENTS

| | | | |
|---|---|---|---|
| 3,812,264 | 5/1974 | Nouel | 424/1 |
| 4,424,200 | 1/1984 | Crockford et al. | 424/1.1 |
| 4,427,646 | 1/1984 | Olexa et al. | 424/1.1 |
| 4,434,151 | 2/1984 | Byrne et al. | 424/1.1 |
| 4,444,690 | 4/1984 | Fritzberg | 260/429 |
| 4,455,290 | 6/1984 | Olexa et al. | 424/1.1 |
| 4,472,509 | 9/1984 | Gansow et al. | 436/548 |
| 4,479,930 | 10/1984 | Hnatowich | 424/1.1 |
| 4,485,101 | 11/1984 | Coy et al. | 424/177 |
| 4,571,430 | 2/1986 | Byrne et al. | 560/148 |
| 4,575,556 | 3/1986 | Byrne et al. | 549/63 |
| 4,668,503 | 5/1987 | Hnatowich | 424/1.1 |
| 4,732,864 | 3/1988 | Tolman | 436/547 |
| 4,810,693 | 3/1989 | Pickart | 514/18 |
| 4,822,606 | 4/1989 | Snyderman et al. | 424/88 |
| 4,853,371 | 8/1989 | Coy et al. | 514/12 |
| 4,861,869 | 8/1989 | Nicolotti et al. | 530/402 |
| 4,871,717 | 10/1989 | Coy et al. | 514/11 |
| 4,877,868 | 10/1989 | Reno et al. | 530/390 |
| 4,904,642 | 2/1990 | Coy et al. | 514/11 |
| 4,986,979 | 1/1991 | Morgan, Jr. et al. | 424/1.1 |
| 4,988,496 | 1/1991 | Srinivasan et al. | 424/1.11 |
| 5,011,676 | 4/1991 | Thakur | 424/1.1 |
| 5,011,916 | 4/1991 | Bonnyman et al. | 534/14 |
| 5,023,237 | 6/1991 | Pickart | 514/18 |
| 5,053,493 | 10/1991 | Pak et al. | 530/402 |
| 5,059,588 | 10/1991 | Pickart | 514/12 |
| 5,061,641 | 10/1991 | Shochat et al. | 436/545 |
| 5,078,985 | 1/1992 | Rhodes | 424/1.11 |
| 5,102,990 | 4/1992 | Rhodes | 530/391.5 |
| 5,116,596 | 5/1992 | Bremer | 424/1.1 |
| 5,118,791 | 6/1992 | Burnier et al. | 530/326 |
| 5,128,119 | 7/1992 | Griffiths | 424/1.1 |
| 5,190,920 | 3/1993 | Eyal et al. | 514/17 |
| 5,328,840 | 7/1994 | Coller | 435/240.2 |
| 5,330,911 | 7/1994 | Hubbell et al. | 435/240.243 |
| 5,376,356 | 12/1994 | Morgan, Jr. | 424/141 |
| 5,443,815 | 8/1995 | Dean et al. | 424/1.41 |
| 5,443,816 | 8/1995 | Zamora et al. | 424/1.69 |
| 5,460,785 | 10/1995 | Rhodes et al. | 424/1.49 |
| 5,556,609 | 9/1996 | Zamora | 424/1.69 |
| 5,567,408 | 10/1996 | Zamora | 424/1.69 |

FOREIGN PATENT DOCUMENTS

| | | |
|---|---|---|
| 2016235 | 11/1990 | Canada. |
| 84109831.2 | 3/1985 | European Pat. Off.. |
| 86100360.6 | 7/1986 | European Pat. Off.. |
| 87300426.1 | 9/1987 | European Pat. Off.. |
| 88104755.9 | 9/1988 | European Pat. Off.. |
| 0359347 | 3/1990 | European Pat. Off.. |
| 90302760.5 | 9/1990 | European Pat. Off.. |
| 0398143 | 11/1990 | European Pat. Off.. |

(List continued on next page.)

OTHER PUBLICATIONS

Babich et al (1993). Technetium—99m Labeled Hydrazino Nicotinamide Derivatized Chemotactic Peptide Analog for Imaging Focalsites of Bacterial Infection. J. Nucl. Med., vol. 34, No. 11, pp. 1964–1974.

(List continued on next page.)

*Primary Examiner*—John Kight
*Assistant Examiner*—Dameron Jones
*Attorney, Agent, or Firm*—Darby & Darby

[57] ABSTRACT

Peptides containing a biological-function domain and a medically useful metal ion-binding domain are labeled with medically useful metal ions for use in diagnosis and treatment of a variety of pathologic conditions. The peptides have the amino acid sequence $$(R_1)-[Y_1]_n-(R_2),$$

$$(R_1)-[Y_1-(R_2)-Y_1]_n-(R_3)$$

and $$(R_1)-[Y_1-(R_2)-Y_2]_n-(R_3)$$

wherein the medically useful metal ion-binding domain is $[Y_1]_n$, $[Y_1-(R_2)-Y_1]_n$ or $[Y_1-(R_2)-Y_2]_n$, in which n is a number between 1 and about 6 and $Y_1$ and $Y_2$ are amino acids with a sulfur, nitrogen or oxygen which is available for binding to metal ions, or can be made available for binding to metal ions; the biological-function domain is an amino acid sequence containing from 1 to about 20 amino acids located in any one or more of $R_1$, $R_2$ or $R_3$; and those portions of $R_1$, $R_2$ and $R_3$ which are not part of the biological-function domain are amino acid sequences containing from 0 to about 20 amino acids. The resulting product may be stored frozen or lyophilized, with labeling accomplished by the addition of the medically useful metal ions. The medically useful metal ion may be radioactive or paramagnetic, with diagnosis performed by gamma scintigraphy, specific photon emission computerized tomography, positron emission tomography or magnetic resonance imaging.

15 Claims, No Drawings

FOREIGN PATENT DOCUMENTS

| | | | |
|---|---|---|---|
| 2043459 | 5/1969 | France | A61K 27/00 |
| 2225579 | 6/1990 | United Kingdom . | |
| WO8807382 | 10/1988 | WIPO . | |
| 89/00051 | 1/1989 | WIPO . | |
| WO 90/15818 | 6/1989 | WIPO | C07K 5/08 |
| WO8904666 | 6/1989 | WIPO . | |
| 89/10760 | 11/1989 | WIPO | A61K 49/02 |
| 90/13317 | 11/1990 | WIPO | A61K 49/02 |
| 9013317 | 11/1990 | WIPO . | |
| 90/15818 | 12/1990 | WIPO | A61K 49/02 |
| WO9015626 | 12/1990 | WIPO . | |
| 91/00111 | 1/1991 | WIPO | A61K 49/02 |
| WO9101144 | 2/1991 | WIPO . | |
| 91/17173 | 11/1991 | WIPO . | |
| WO9213572 | 8/1992 | WIPO | A61K 49/02 |
| 9312819 | 7/1993 | WIPO . | |
| 9323085 | 11/1993 | WIPO . | |
| 9325244 | 12/1993 | WIPO . | |
| WO940089 | 1/1994 | WIPO | C07K 7/26 |
| WO 95/11045 | 10/1994 | WIPO | A61K 51/08 |
| 9501188 | 1/1995 | WIPO . | |
| WO950330 | 2/1995 | WIPO | C07K 14/655 |

OTHER PUBLICATIONS

Zamora et al (1993). Biological Distribution of 99m—Tc Labeled YIGSR and IKVAV Laminin Peptides in Rodents: 99m–Tc–IKVAV Peptide Localizes to the Lungs. Biochim. Biophys. Acta, vol. 1182, No. 2, pp. 197–204.

Zamora et al (1992). Imidazdes as Well as Thioates in Proteins Bind Technetium—99m Bioconjugate Chemistry, vol. 3, No. 6, pp. 493–498.

N. Bryson, et al., "Neutral Technetium (V) Complexes with Amide–Thiol–Thioether Chelating Ligands," Inorg. Chem., vol. 27, pp. 2154–2161, 1988.

N. Bryson, et al., "Protecting Groups in the Preparation of Thiolate Complexes of Technetium," Inorg. Chem., vol. 29, pp. 2948–2951, 1990.

E.F. Byrne, et al., "Technetium—99m Bifunctional Chelating Agent—Thiolacctone for Coupling to Biomolecules, $N_2S2$ Ligand for Chelation to Technetium," The Journal of Nuclear Medicine, vol. 24, p. 126, 1983.

D.W. Cox, et al., "Technetium Labelled Somatostatin a Potential Agent for In Vivo Tumour Localisation," 7th International Symposium on Radiopharmacology, Abstract, p. 16, 1991.

A. Davidson, et al., "A New Class of Oxotechnetium (5+) Chelate Complexes Containing a $TcON_2S_2$ Core," Ingor. Chem., vol. 20, No. 6, 1981.

A. R. Fritzberg, et al., "Synthesis and Biological Evaluation of Tc—99m N,N'–Bis(mercaptoacetyl)–2,3–diaminopropanoate: A Potential Replacement for $[^{131}I]$o–iodohippurate," The Journal of Nuclear Medicine, vol. 23, pp. 592–598, 1982.

B.A. Khaw, et al., "Technetium—99m Labeling of Antibodies to Cardiac Myosin Fab and to Human Fibrinogen," The Journal of Nuclear Medicine, vol. 23, pp. 1011–1019, 1982.

D.J. Kwekkeboom, et al., "$[^{In-111-DTPA-D-Phe}]_1$–Octreotide Scintigraphy in Neuro–Endocrine Tumors," The Journal of Nuclear Medicine, vol. 32, No. 5, p. 981, 1991.

B.A. Rhodes, "Considerations in the Radiolabeling of Albumin," Seminars in Nuclear Medicine, vol. 4, No. 3, pp. 281–293, 1974.

"The Labeling of High Affinity Sites of Antibodies with 99mTc," by Chang H. Paik et al., Int. J. Nucl. Med. Biol., vol. 12, No. 1, pp. 3–8 (1985).

"Technetium—99m Labeling of Murine Monoclonal Antibody Fragments," by Buck A. Rhodes et al., J. Nucl. Med., vol. 27, No. 5, pp. 685–693 (May 1986).

Arnold, Frances H., et al., "Engineered Metal–Binding Proteins: Purification to Protein Folding," Science, vol. 252, pp. 1796–1797 (Jun. 28, 1991) Cioce, Vittoria, et al., Increased Expression of the Laminin Receptor in Human.

Castronovo, Vincent, et al., "Laminin Receptor Complementary DNA–deduced Synthetic Peptide Inhibits Cancer Cell Attachment to Endothelium," Cancer Research, vol. 51, pp. 5672–5678 (Oct. 15, 1991).

Colon Cancer, Articles, Journal of National Cancer Institute, vol. 83, No. 1, pp. 29–36 (Jan. 2, 1991).

Fischman, Alan J., et al., "Imaging Focal Sites of Bacterial Infection in Rats with Indium–111–Labeled Chemotactic Peptides Analogs," Journal of Nucl. Med., vol. 32, No. 3, pp. 483–491 (Mar. 1991).

Ghadiri, M. Reza, et al., "Peptide Architecture, Design of Stable α–Helical Metallopeptides via a Novel Exchange–Inert $Ru^{III}$ Complex," J. Am. Chem. Soc., vol. 112, No. 26, pp. 9633–9635 (1990).

Hynes, Richard O., "Integrins: A Family of Cell Surface Receptors," Review, Cell, vol. 48, pp. 549–554 (1987).

Iverson, Brent L., et al., "Metalloantibodies," Reports, Science, vol. 249, pp. 659–662 (Aug. 1990).

Janeczek, Amelia H., et al., "Autoradiographic analysis of formylpeptide chemoattractant binding, uptake and intracellular processing by neutrophils," Journal of Cell Science, vol. 94, pp. 155–168 (1989).

Kwekkeboom, Dirk J., et al., "Radioiodinated Somatostatin Analog Scintigraphy in Small–Cell Lung Cancer," Journal of Nucl. Med., vol. 32, No. 10, pp. 1845–1848 (Oct. 1991).

Seifert, S., et al., "Technetium—99m and 99m chelates with N–donor ligands: a new class of potential cationic radiopharmaceuticals," Technitium in Chemistry and Nuclear Medicine, E. Deutsch, M. Nicolini, H.N. Wagner, Jr., eds., Cortina International, Verona, pp. 19–23 (1983).

Sonnenberg, Arnoud, et al., Laminin receptor on platelets is the integrin VLA–6, Nature, vol. 336, pp. 487–489 (Dec. 1988).

Tandon, Narendra N., et al., "Interaction of human platelets with laminin and identification of the 67 kDa laminin receptor on platelets," Biochem. J., vol. 274, pp. 535–542 (1991).

Thompson, H.L., et al., "Identification of an amino acid sequence in the laminin A chain mediating mast cell attachment and spreading," Immunol., vol. 72, pp. 144–149 (1991).

Vallee, Bert L., et al., "Zinc Coordination, Function, and Structure of Zinc Enzymes and Other Proteins," Biochemistry, vol. 29, No. 24, pp. 5647–5659 (Jun. 19, 1990).

W.H. Bakker, et al., "In Vivo Use of a Radioiodinated Somatostatin Analogue: Dynamics, Metabolism, and Binding to Somatostatin Receptor–Positive Tumors in Man," The Journal of Nuclear Medicine, vol. 32, No. 6, pp. 1184–1191, 1991.

W.H. Bakker, et al., "Receptor Scintigraphy with a Radioiodinated Somatostatin Analogue: Radiolabeling, Purification, Biologic Activity, and In Vivo Application in Animals," The Journal of Nuclear Medicine, vol. 31, pp. 1501–1509, 1990.

Albert R. Bakker W. Pless J. et al: A Somatostatin Analogue to Image SS–Receptor–Positive Tumours: [$^{111}$In–DTPA–D-Phe]$^1$–Octreotide (SDZ 215–811).*J. Nuc. Med.*, vol. 31, 1990 (Abstract).

Kwekkeboom DJ, Oei HY, Bakker WH, et al: [In–111–DPTA–D–Phe]–Octreotide Scintigraphy In Neuro–Endocrine Tumors. *J. Nuc. Med.* 32:981, 1991 (Abstract).

Cox et al: Technetium Labeled Somatostatin A Potential Agent For In Vivo Tumour Localization. 7th International Symposium on Radiopharmacology, (1991), p. 16.

Tubis M, Endow JS: The Preparation of $^{99m}$Technetium—Labeled Cystine, Methionine and a Synthetic Polypeptide and their Distribution in Mice. *Int. J. Appl. Rad. and Isotopes* 19:835–840, 1968.

SEQUENCE LISTING ( 1 ) GENERAL INFORMATION:

( i i i ) NUMBER OF SEQUENCES: 7

( 2 ) INFORMATION FOR SEQ ID NO: 1

( i ) SEQUENCE CHARACTERISTICS:

( A ) LENGTH: 5 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 1:

Tyr  Ile  Gly  Ser  Arg
        1                            5

( 2 ) INFORMATION FOR SEQ ID NO: 2

( i ) SEQUENCE CHARACTERISTICS:

( A ) LENGTH: 9 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 2:

Cys  Asp  Pro  Gly  Tyr  Ile  Gly  Ser  Arg
        1                            5

( 2 ) INFORMATION FOR SEQ ID NO: 3

( i ) SEQUENCE CHARACTERISTICS:

( A ) LENGTH: 3 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 3:

Met  Leu  Phe
         1

( 2 ) INFORMATION FOR SEQ ID NO: 4

( i ) SEQUENCE CHARACTERISTICS:

( A ) LENGTH: 4 amino acids
           ( B ) TYPE: amino acid
           ( C ) STRANDEDNESS: single
           ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 4:

Met  Ile  Phe  Leu
         1

( 2 ) INFORMATION FOR SEQ ID NO: 5

( i ) SEQUENCE CHARACTERISTICS:

( A ) LENGTH: 2 amino acids
           ( B ) TYPE: amino acid
           ( C ) STRANDEDNESS: single
           ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 5:

Met  Ala
         1

( 2 ) INFORMATION FOR SEQ ID NO: 6

( i ) SEQUENCE CHARACTERISTICS:

( A ) LENGTH: 13 amino acids
           ( B ) TYPE: amino acid
           ( C ) STRANDEDNESS: single
           ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 6:

Met  Leu  Phe  Gly  His  Gly  Gly  His  Gly  His  Gly  Gly  His
     1               5                               10

( 2 ) INFORMATION FOR SEQ ID NO: 7

( i ) SEQUENCE CHARACTERISTICS:

( A ) LENGTH: 4 amino acids
           ( B ) TYPE: amino acid
           ( C ) STRANDEDNESS: single
           ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 7:

Phe Trp Lys Thr
1

PEPTIDE-METAL ION PHARMACEUTICAL PREPARATION

CROSS-REFERENCE TO RELATED APPLICATIONS

This is a divisional of application Ser. No. 07/840,077, filed Feb. 20, 1992, now U.S. Pat. No. 5,443,816, issued Aug. 22, 1995, which is a continuation-in-part application of U.S. patent application Ser. No. 07/565,275, filed Aug. 8, 1990, now U.S. Pat. No. 5,102,990, issued Apr. 7, 1992, entitled Direct Radiolabeling of Antibodies and Other Proteins with Technetium or Rhenium; and is related to U.S. Pat. No. 5,078,985, issued Jan. 7, 1992 entitled Radiolabeling Antibodies and Other Proteins with Technetium or Rhenium by Regulated Reduction; U.S. patent application Ser. No. 07/816,476, filed Jan. 3, 1992, now U.S. Pat. No. 5,46,687, issued Sep. 13, 1994, entitled Direct Radiolabeling of Antibody Against Stage Specific Embryonic Antigen for Diagnostic Imaging now U.S. Pat. No. 5,346,687, issued Sep. 13, 1994; and U.S. patent application Ser. No. 07/816,477, filed Jan. 3, 1992, now U.S. Pat. No. 5,460,785, issued Oct. 24, 1995 entitled Direct Labeling of Antibodies and Other Proteins with Metal Ions now U.S. Pat. No. 5,460,785, issued Oct. 24, 1995; the teachings of all of the foregoing are incorporated herein by reference. A related application entitled Ser. No. 07/840,076, filed Feb. 20, 1992, now U.S. Pat. No. 5,277,892, issued Jan. 11, 1994, entitled in Vivo Lymphocyte Tagging, was filed concurrently herewith, and the specification thereof is incorporated herein by reference.

LICENSE RIGHTS

The U.S. Government has a paid-up license in this invention and the right in limited circumstances to require the patent owner to license others on reasonable terms as provided for by the terms of Small Business Innovative Research Grant No. 2 R44 CA50877 awarded by the National Cancer Institute, Department of Health and Human Services.

BACKGROUND OF THE INVENTION

1. Field of the Invention (Technical Field)

This invention relates to peptide-based metal ion-labeled compositions for use as pharmaceuticals, and methods of labeling peptides, proteins and other similar substances with radiometals, paramagnetic metals and other medically useful metal ions, and further providing for use of medically useful metal ion-labeled peptides for detection of thrombus, cancer, infection and inflammation.

2. Description of the Related Art, Including Information Disclosed under 37 C.F.R. Sections 1.97–1.99 (Background Art)

The use of proteins, particularly antibodies, as biologically active targeting agents for medically useful metal ions has been explored. These products can be administered to the human body to visualize or monitor functioning of various parts of the body or to determine the presence and location of particular antigens, antibodies, hormones or the like; and can be used in the treatment of various disease states. Antibodies and antibody fragments have been labeled with a number of radionuclides for use in clinical diagnosis. Radionuclides commonly used include $^{131}I$, $^{125}I$, $^{123}I$, $^{99m}Tc$, $^{67}Ga$, and $^{111}In$ for diagnostic imaging; and radionuclides such as $^{90}Y$, $^{188}Re$, and $^{186}Re$, and to a lesser extent, $^{199}Au$, $^{131}I$ and $^{67}Cu$ for targeted therapy, primarily in the treatment of cancer. There are also useful metals for magnetic resonance imaging, including gadolinium, manganese, copper, iron, gold and europium, which are not radioisotopes. So far, limited work has been done with labeling with positron-emitting radiometals, although some types of proteins, such as transferrin and human serum albumin, have been labeled with $^{68}Ga$.

Two primary methods have been employed to label antibodies with radiometals, with particular emphasis having been placed on radiolabeling with $^{99m}Tc$. In one method, bifunctional chelates are conjugated to the antibody, and the bifunctional chelate is then radiolabeled. A variety of bifunctional chelates have been employed; most involve metal ion binding to thiolate groups, and may also involve metal ion binding to amide, amine or carboxylate groups. Representative bifunctional chelates include ethylenediamine tetraacetic acid (EDTA), diethylenetetramine-pentaacedic acid (DTPA), chelates of diamide-dimercaptides ($N_2S_2$), and variations on the foregoing, such as chelating compounds incorporating $N_2S_3$, $N_2S_4$ or $N_3S_3$ metal binding sites, and metallothionine. The alternative method of radiolabeling antibodies involves reduction of disulfide bonds in the protein, with subsequent binding of the metal ion to thiolate groups. A variety of reducing agents have been employed, including stannous salts, dithiothreitol and 2-mercaptoethanol.

The use of biologically active peptides, which are peptides which bind to specific cell surface receptors, has received some consideration as radiopharmaceuticals. Canadian Patent Application 2,016,235, Labeled Chemotactic Peptides to Image Focal Sites of Infection or Inflammation, teaches a method of detecting a site of infection or inflammation, and a method for treating such infection or inflammation, by administration of a labeled or therapeutically-conjugated chemotactic peptide. In this application, the chemotactic peptides are chemically conjugated to DTPA and subsequently labeled with $^{111}In$. The utility of DTPA chelates covalently coupled to polypeptides and similar substances is well known in the art. Hnatowich, D. J., U.S. Pat. Nos. 4,479,930 and 4,668,503. Other bifunctional chelates for radiolabeling peptides, polypeptides and proteins are well known in the art. Other biologically active peptides described include that disclosed by Olexa S. A., Knight L. C. and Budzynski AZ, U.S. Pat. No. 4,427,646, Use of Radiolabeled Peptide Derived From Crosslinked Fibrin to Locate Thrombi In Vivo, in which iodination is discussed as a means of radiolabeling. In Morgan C. A. Jr. and Anderson D. C., U.S. Pat. No. 4,986,979, Imaging Tissue Sites of Inflammation, use of chelates and direct iodination is disclosed. In Tolman G. L., U.S. Pat. No. 4,732,864, Trace-Labeled Conjugates of Metallothionein and Target-Seeking Biologically Active Molecules, the use of metallothionein or metallothionein fragments conjugated to a biologically active molecule, including peptides, is disclosed. The previous methods all employ some conjugation means with a bifunctional chelator in order to effectuate labeling with a radionuclide or other medically useful metal ion, such as a paramagnetic contrast agent. The only exception involves radioiodination; the iodine labeling of proteins or peptides containing tyrosine or histidine residues is well known, for example, by the chloramine-T, iodine monochloride, Iodogen or lactoperoxidase methods.

The potential role of amino acid sequences found in peptides and proteins in binding transition metals has been recognized. In Vallee BL and Auld DS: Zinc coordination, function, and structure of zinc enzymes and other proteins, *Biochemistry* 29:5648–5659, 1990, the general characteristics of non-metallothionein proteins which contain zinc binding sites are described. Arnold FH and Haymore BL describe histidine-containing amino acid sequences used for protein purification by metal-chelate chromatography (Engineered metal-binding proteins: purification to protein folding. *Science* 252:1796–1797, 1991). Iverson et al. describe a means of genetic manipulation of antibodies to contain metal binding sites in the immunological binding region with the goal of producing catalytic antibodies (Iverson B. L., Iverson S. A., Roberts V. A., Getzoff E. D., Tainer J. A., Benkovic S. J. and Lerner R. A.: Metalloantibodies, *Science* 249:659–662, 1990). The use of histidine-containing amino acid sequences which bind Ru to form exchange-inert metal complexes to form highly stable α-helical metallopeptides was described in Ghardiri M. R. and Fernholz A. K.: Peptide architecture. Design of stable α-helical metallopeptides via a novel exchange-inert $Ru^{111}$ complex. *J Am Chem Soc* 112:9633–9635, 1990. The role of isolated amino acid ligands to bind $^{99}Tc$ and $^{99m}Tc$ has long been recognized; Seifert et al. describes the capability of nitrogen donor atoms to stabilize reduced technetium species using free lysine, ornithine and histidine (Seifert S., Munze R. and Johannsen B.: Technetium-99 and 99m chelates with N-donor ligands: a new class of potentially cationic radiopharmaceuticals, in Technetium in Chemistry and Nuclear Medicine Deutsch E, Nicolini M. and Wagner H. N. Jr., eds., Cortina International, Verona, 1983, pp 19–23. Similarly, use of free cysteine, cystine and penicillamine to bind $^{99m}Tc$ is known by those skilled in the art.

SUMMARY OF THE INVENTION (DISCLOSURE OF THE INVENTION)

In accordance with the present invention, a peptide-based pharmaceutical composition suitable for administration to a patient is provided. The composition, which may be lyophilized, includes a peptide which itself comprises a biological-function domain and a medically useful metal ion-binding domain, and further includes a metal ion labeling agent. The peptide is selected from the group consisting of

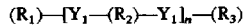

and

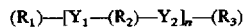

wherein, the medically useful metal ion-binding domain is selected from one of the group consisting of $[Y_1]_n$, $[Y_1$-$(R_2)$-$Y_1]_n$ and $[Y_1$-$(R_2)$-$Y_2]_n$ in which n is a number between 1 and about 6 and $Y_1$ and $Y_2$ are amino acids comprising a sulfur, nitrogen or oxygen which is available for binding to metal ions, or can be made available for binding to metal ions;

the biological-function domain comprises at least one of the group consisting of $R_1$, $R_2$ and $R_3$ and further comprises an amino acid sequence containing from 1 to about 20 amino acids; and those portions of $R_1$, $R_2$ and $R_3$ not comprising the biological-function domain each comprise an amino acid sequence containing from 0 to about 20 amino acids.

The biological-function domain may be located in any one or more of $R_1$, $R_2$ or $R_3$, including situations in which the biological-function domain comprises all or part of two or more of $R_1$, $R_2$ or $R_3$. It is not required that the biological-function domain constitute all of the amino acid sequence of any one of $R_1$, $R_2$ or $R_3$; that is, it is possible and contemplated that the biological-function domain will be an amino acid sequence constituting a portion of the total amino acid sequence of any one of $R_1$, $R_2$ or $R_3$, with the remainder of that region being an amino acid sequence which is not the biological-function domain.

The medically useful metal ion-binding domain of the peptide-based pharmaceutical composition includes amino acid sequences containing cysteine, cystine, histidine, penicillamine, deacylated methionine, lysine, arginine, aspartic acid, glutamic acid or tyrosine. Specific medically useful metal ion-binding domains include the following:

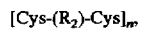

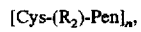

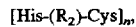

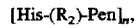

and

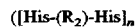

wherein, n is a number between 1 and about 6; and $R_2$ is an amino acid sequence containing from 1 to about 20 amino acids. $R_2$ may optionally include all or part of the biological-function domain, or the biological-function domain may be located outside of the metal ion-binding domain.

The metal ion labeling agent which is included in the peptide-based pharmaceutical composition can be a stannous ion agent, which may be present in a solution including alkali metal tartrate. The stannous ion agent can also be present in a solution including dicarboxylic acid. Representative forms of dicarboxylic acid which can be used include phthalate, tartrate and citrate. The stannous ion agent itself can include stannous tartrate, stannous glucoheptonate, stannous gluconate, stannous phosphonate, stannous chloride or stannous fluoride.

The peptide-based pharmaceutical composition can also include a medically useful metal ion, which may be radioactive or paramagnetic. The medically useful metal ion can be selected from the group consisting of ionic forms of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine. The medically useful metal ion can also be a radionuclide comprising an isotope selected from the group consisting of indium, gold, silver, mercury, technetium, rhenium and copper.

The invention also discloses a method of performing a diagnostic procedure in a patient, in which a patient is administered a medically useful metal ion-labeled peptide in an amount effective for imaging, with the peptide including a biological-function domain and a metal ion-binding domain, followed by imaging by metal ion detection means. The peptide with a biological-function domain and a metal ion-binding domain can be selected from the group consisting of $(R_1)$—$[Y_1]_n$—$(R_2)$, $(R_1)$—$[Y_1$—$(R_2)$—$Y_1]_n$—$(R_3)$ and $(R_1)$—$[Y_1$—$(R_2)$—$Y_2]_n$—$(R_3)$ wherein, the medically useful metal ion-binding domain is selected from one of the group consisting of $[Y_1]_n$, $[Y_1\text{-}(R_2\text{-}Y_1]_n$ and $[Y_1\text{-}(R_2)\text{-}Y_2]_n$ in which n is a number between 1 and about 6 and $Y_1$ and $Y_2$ are amino acids comprising a sulfur, nitrogen or oxygen which is available for binding to metal ions, or can be made available for binding to metal ions;

the biological-function domain comprises at least one of the group consisting of $R_1$, $R_2$ and $R_3$ and further comprises an amino acid sequence containing from 1 to about 20 amino acids; and those portions of $R_1$, $R_2$ and $R_3$ not comprising the biological-function domain each comprise an amino acid sequence containing from 0 to about 20 amino acids.

Here too the biological-function domain may be located in any one or more of $R_1$, $R_2$ or $R_3$, including situations in which the biological-function domain comprises all or part of two or more of $R_1$, $R_2$ or $R_3$. It is not required that the biological-function domain constitute all of the amino acid sequence of any one of $R_1$, $R_2$ or $R_3$; that is, it is possible and contemplated that the biological-function domain will be an amino acid sequence constituting a portion of the total amino acid sequence of any one of $R_1$, $R_2$ or $R_3$, with the remainder of that region being an amino acid sequence which is not the biological-function domain.

The medically useful metal ion-binding domain of the peptide used in this method includes amino acid sequences containing cysteine, cystine, histidine, penicillamine, deacylated methionine, lysine, arginine, aspartic acid, glutamic acid or tyrosine. Specific medically useful metal ion-binding domains include the following:

$[\text{Cys}]_n$, $[\text{Cys-}(R_2)\text{-Cys}]_n$, $[\text{Cys-}(R_2)\text{-Pen}]_n$, $[\text{His-}(R_2)\text{-Cys}]_n$, $[\text{His-}(R_2)\text{-Pen}]_n$, $[\text{His}]_n$ and $([\text{His-}(R_2)\text{-His}]_n$ wherein, n is a number between 1 and about 6; and $R_2$ is an amino acid sequence containing from 1 to about 20 amino acids. $R_2$ may optionally include all or part of the biological-function domain, or the biological-function domain may be located outside of the metal ion-binding domain.

The type of metal ion detection imaging used in the method includes gamma scintigraphy, specific photon emission computerized tomography, positron emission tomography and magnetic resonance imaging.

The medically useful metal ion used in the method may be radioactive or paramagnetic, and includes ionic forms of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine. The medically useful metal ion may also be a radionuclide comprising a member selected from the group consisting of isotopes of indium, gold, silver, mercury, technetium, rhenium and copper.

The method may be accomplished by parenteral administration of the medically useful metal ion-labeled peptide. Such parenteral administration may be by intradermal, subcutaneous, intramuscular, intraperitoneal or intravenous injection.

The method can be applied for the diagnostic procedure of detecting a site of metastatic cancer, wherein the biological-function domain of the peptide comprises an amino acid sequence including Tyr-Ile-Gly-Ser-Arg (SEQ. ID NO. 1). The peptide, including the metal ion-binding domain, can be $H_2N$-Cys-Asp-Pro-Gly-Tyr-Ile-Gly-Ser-Arg-OH derived from SEQ. ID NO. 2) or $H_2N$-Cys-Asp-Pro-Gly-Tyr-Ile-Gly-Ser-Arg-$NH_2$.

The method can also be applied for the diagnostic procedure of detecting a site of thrombus, wherein the biological-function domain of the peptide comprises an amino acid sequence including Tyr-Ile-Gly-Ser-Arg. The peptide, including the metal ion-binding domain, can be $H_2N$-Cys-Asp-Pro-Gly-Tyr-Ile-Gly-Ser-Arg-OH or $H_2N$-Cys-Asp-Pro-Gly-Tyr-Ile-Gly-Ser-Arg-$NH_2$.

The method can also be applied for the diagnostic procedure of detecting a site of infection or inflammation, wherein the biological-function domain of the peptide comprises an amino acid sequence which is N-formyl-Met-Leu-Phe (derived from SEQ. ID NO. 3), N-formyl-Met-Ile-Phe-Leu or (derived from SEQ. 4) N-formyl-Met-Ala (derived from SEQ. ID NO. 5).

The method can also be applied for the diagnostic procedure of detecting a site of cancer, wherein the biological-function domain of the peptide comprises an amino acid sequence including Phe-Trp-Lys-Thr (SEQ. ID NO. 7) and the metal ion-binding domain contains at least one disulfide bridge which has been reduced, with a source of stannous ion agent complexed to the resulting thiolates.

The invention also discloses a method of labeling a peptide containing at least one disulfide bond with a medically useful metal ion to obtain stable labeling, in which the peptide is incubated with a first reducing agent, the period of incubation being sufficient to reduce available disulfide bonds to thiolate groups while preventing excessive fragmentation of the peptide; the first reducing agent is substantially removed from the thiolate-containing peptide; a source of Sn (II) agent is added to the thiolate-containing peptide in a sufficient amount to form Sn (II)-containing and sulfur-containing complexes; and the Sn (II)-containing and sulfur-containing complexes is labeled by adding the medically useful metal ion, whereby the medically useful metal ion displaces the Sn (II) agent and the medically useful metal ion and thiolate-containing peptide form medically useful metal ion-containing and sulfur-containing complexes. The order of the steps may be altered, and the method will still produce metal ion-labeled peptides. Specifically, it is possible, and in some cases advantageous, to add the Sn (II) to form Sn (II)-containing and sulfur-containing complexes prior to removing excess reducing agent from the thiolate-containing peptide. In this way, oxidation of thiolate groups or reformation of disulfide bonds and other cross-linkages can be minimized.

The first reducing agent can include 2-mercaptoethanol; 1,4-dithiothreitol; 2,3-dihydroxybutane-1,4-dithiol;

2-aminoethanethiol HCl; 2-mercaptoethylamine; thioglycolate; cyanide; cysteine; reduced glutathione; Sn (II); Cu (I); and Ti (II). It is possible to attach the first reducing agent to a solid phase.

The source of Sn (II) agent can include stannous tartrate, stannous glucoheptonate, stannous gluconate, stannous phosphonate, stannous chloride, and stannous fluoride. Following addition of the source of Sn (II) agent, a second reducing agent can be added to the Sn (II)-containing and sulfur-containing complexes in a sufficient amount to reduce the oxidation state of the medically useful metal ion to a state whereby the medically useful metal ion displaces the Sn (II) agent and the metal ion and thiolate-containing peptide forms medically useful metal ion-containing and sulfur-containing complexes. This second reducing agent can be any of the Sn (II) agents listed above. It is also possible to initially add sufficient Sn (II) agent to reduce the oxidation state of the medically useful metal ion as set forth above. The source of Sn (II) agent can be present in a solution including alkali metal tartrate having a pH of between approximately 5.0 and 6.0. A variety of dicarboxylic acids can be added to the Sn (II) agent, including phthalate, tartrate or citrate. The thiolate-containing peptide can be in a solution which includes free amino acids, such as glycine.

After adding the Sn (II) agent, the Sn (II)-containing and sulfur-containing complexes can be frozen in a vial, and maintained for an indefinite period before labeling by the addition of the medically useful metal ion to the vial. Similarly, after addition of the Sn (II) agent, the product can be lyophilized in a vial, and maintained for an indefinite period before labeling.

The medically useful metal ion can be radioactive or paramagnetic. Medically useful metal ions include ionic forms of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine. Some medically useful metal ions are radionuclides, such as isotopes of indium, gold, silver, mercury, technetium, rhenium and copper.

The product resulting from the application of this method can be used for gamma scintigraphy, specific photon emission computerized tomography, magnetic resonance imaging, positron emission tomography or radiotherapy.

The invention further also discloses a method of labeling a peptide containing at least one amino acid selected from the group consisting of amino acids containing sulfur, nitrogen or oxygen with a medically useful metal ion to obtain stable labeling, in which the peptide is incubated with a source of Sn (II) agent in a sufficient amount to form Sn (II)-containing and sulfur- or nitrogen- or oxygen-containing complexes; and the Sn (II)-containing and sulfur- or nitrogen- or oxygen-containing complexes is labeled by adding the medically useful metal ion, whereby the medically useful metal ion displaces the Sn (II) agent and the medically useful metal ion and sulfur- or nitrogen- or oxygen-containing peptide form medically useful metal ion-containing and sulfur- or nitrogen- or oxygen containing complexes. The amino acids containing sulfur, nitrogen or oxygen can be Cys, Pen, Met, His, Lys, Arg, terminal amino group, Asp, Glu, Tyr, or the terminal carboxyl group. The source of Sn (II) agent can be stannous tartrate, stannous glucoheptonate, stannous gluconate, stannous phosphonate, stannous chloride or stannous fluoride.

After addition of the Sn (II) agent, a reducing agent can be added to the Sn (II)-containing and sulfur- or nitrogen-containing complexes in a sufficient amount to reduce the oxidation state of the medically useful metal ion to a state whereby the medically useful metal ion displaces the Sn (II) agent and the metal ion and sulfur- or nitrogen-containing peptide forms metal ion-containing and sulfur- or nitrogen-containing complexes. The reducing agent can be stannous tartrate, stannous glucoheptonate, stannous gluconate, stannous phosphonate, stannous chloride, or stannous fluoride. The source of Sn (II) agent can be present in a solution including alkali metal tartrate having a pH of between approximately 5.0 and 6.0. A variety of dicarboxylic acids can be added to the Sn (II) agent, including phthalate, tartrate or citrate. The thiolate-containing peptide can be in a solution which includes free amino acids, such as glycine.

After adding the Sn (II) agent, the Sn (II)-containing and sulfur-containing complexes can be frozen in a vial, and maintained for an indefinite period before labeling by the addition of the medically useful metal ion to the vial. Similarly, after addition of the Sn (II) agent, the product can be lyophilized in a vial, and maintained for an indefinite period before labeling.

The medically useful metal ion can be radioactive or paramagnetic. Medically useful metal ions include ionic forms of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine. Some medically useful metal ions are radionuclides, such as isotopes of indium, gold, silver, mercury, technetium, rhenium and copper.

The product resulting from the application of this method can be used for gamma scintigraphy, specific photon emission computerized tomography, magnetic resonance imaging, positron emission tomography or radiotherapy.

Accordingly, it is an object of the present invention to provide for pharmaceutically useful peptides comprising a biological-function domain and a medically useful metal ion-binding domain.

It is a further object of the present invention to provide a means whereby diseases can be diagnosed or treated.

It is a further object of the present invention is to provide a means whereby metal ion-binding domains can be directly synthesized or genetically introduced into a peptide, thereby allowing labeling without the necessity of conjugation to bifunctional chelators.

Another object of the present invention to provide a method for performing a diagnostic procedure by administration of a metal ion-labeled peptide composed of a biological-function domain and a metal ion-binding domain.

Another object of the present invention is to provide a method for the direct labeling of peptides containing disulfide bonds.

Another object of the present invention is to provide a method for the direct labeling of peptides with amino acid sequences containing amino acids with sulfur, nitrogen or oxygen which is available or can be made available for binding metal ions, such as cysteine, histidine or penicillamine, or some combination thereof.

Another object of the present invention is to provide amino acid sequences which bind metal ions, and which can be incorporated into peptides.

It is a further object of the present invention to provide a method to label peptides with medically useful metal ions without loss of the biological function of the peptide due to the labeling process.

Another object of the present invention is to provide a method and product which permits labeling to be accomplished by the end user using a single vial, containing a peptide with a biological-function domain and a medically useful metal ion binding domain and a metal ion labeling agent, which method requires only a single step to accomplish labeling, being the introduction of the medically useful metal ion.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS OF THE INVENTION (BEST MODES FOR CARRYING OUT THE INVENTION)

Using the methods of this invention, peptides containing metal ion binding sequences can be coupled directly with metal ions to provide materials useful for in vivo diagnostic and therapeutic applications. The peptides may be used alone, in combination with other peptides or may be chemically-conjugated to a host molecule. The peptides can be prepared in a format providing a labeling kit which can, in turn, be used to prepare a metal ion-peptide complex for in vivo use. The peptides of this invention contain:

a) biological-function domains, and b) metal ion-binding domains which can complex with medically useful metal ions.

The biological-function domain of the peptide is defined in the specification and claims as a sequence of one or more amino acids which exhibit binding to a biological receptor found on cells, tissues, organs or fluids. The peptides may or may not transmit a signal to the cells, tissues or other materials associated with the biological receptor after binding. The biological-function domain also includes a sequence of one or more amino acids which exhibit binding to a biological receptor found on other peptides, enzymes, antibodies or similar proteinaceous compositions which may themselves exhibit binding to another biological receptor.

The metal ion-binding domain of the peptide is defined in the specification and claims as a sequence of one or more amino acids containing sulfur, nitrogen or oxygen which is available for binding or can be made available for binding to metal ions. Sulfur-containing amino acids include primarily cysteine (Cys), cystine (Cys-Cys) and penicillamine (Pen), although deacylated methionine (Met) may also be used. Nitrogen-containing amino acids include primarily histidine (His), but under certain conditions lysine (Lys) and arginine (Arg), which have $pK_a$ values of 10.0 and 12.0, may also be employed. In addition, the terminal amino group of peptides may also be employed. Oxygen-containing amino acids include aspartic acid (Asp), glutamic acid (Glu) and tyrosine (Tyr), as well as the terminal carboxyl group of peptides. The amino acid sequences most usefully employed will include one or more Cys, one or more His, or a combination of Cys and His. Pen, which is an analogue of Cys, may be directly substituted for any given Cys. Cys may be present in the peptide as a disulfide in the form of cystine. The metal ion-binding domains may occur once or multiple times in any given peptide, and may occur in any combination. The metal ion-binding domain and the biological-function domain may overlap.

The metal binding sequences as found in the peptides of this invention are stabilized by the addition of a positively-charged transition metal ion of Zn, Cu, Sn, Co, or Ni, selected to have a low order of binding strength. Through a replacement reaction, the transition metal ion replaces the H ion of the thiolate, imidazole or carboxyl group. The divalent ions of zinc and tin are thought to be particularly attractive. Some transition metals can simultaneously be used to reduce disulfide bridges and stabilize the metal binding sequences, such as Sn (II), which is particularly useful with cystine formations. In any case, the transition metals are weakly associated with the peptide.

The positively-charged transition metal ions are introduced to the peptide in an aqueous solution containing an appropriate buffer. The buffer may consist of dicarboxylic acids (tartrate, phthalate, citrate), amino acids (glycine), borate or the like. For radiolabeling in acidic conditions typically 10 mM tartrate and 40 mM phthalate, pH 5.6, are used. For radiolabeling in basic conditions typically 10 mM glycine, pH 9.0, is used. The buffer may also contain a number of excipients and/or stabilizers including NaCl, inositol, glucoheptonate, or the like.

The peptides are subsequently incubated with a medically-useful metal ion. The medically-useful metal ion is selected to have a higher order of binding than the positively charged-transition metal ion used to stabilize the metal binding sequences. A number of medically-useful metal ions can be used; radiometals include isotopes of the elements of Tc, Re, Au, Ag, Pd, As, Cu, Hg, and Ru. Radioisotopes of Tc are of significant interest, and particularly $^{99m}$Tc. In the case of $^{99m}$Tc, the peptides are reacted with sodium pertechnetate which has been treated with a reducing agent to generate Tc with a lower oxidation state. The product of the reaction between the metal ion and the peptide is a complex of the metal ion and the peptide. For example, the following structures could result from use of the invention, using Tc labeling of peptides containing metal-ion binding domains consisting of Cys and His groups as an example:

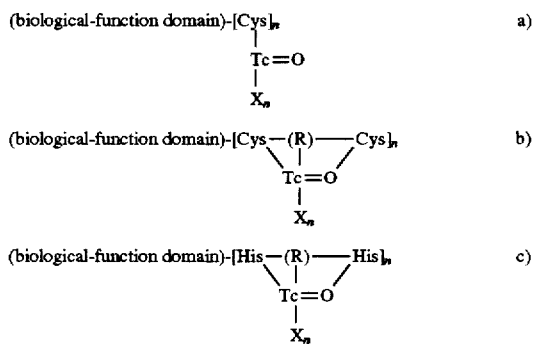

in which R is an amino acid sequence containing from 0 to about 20 amino acids and $X_n$ is an anion, such as a halogen like fluoride or chloride, or a solvent molecule, such as water.

The resulting Tc-peptide bond should have a sufficiently high bond strength to minimize the exchange of the radionuclide to transferrin and serum albumin. The complex should be thermodynamically stable under physiological conditions and exhibit acceptable toxicological properties.

Most stannous reductions are performed at a pH of from about 5 to about 6. With amino acid side chains in a solution at pH 5.6, the basic amino acids are positively charged, the acidic amino acids are largely negatively charged, the alcoholic amino acids are neutral, and methionine is neutral. Since reduced technetium binds more readily to neutral hydrogen donors rather than positively charged hydrogen donors, at the pH range 5 to 6 only Cys and His are optimal $^{99m}$Tc binding site candidates. For both Cys and His, radiolabeling yields are dependant on pH, and are theoretically optimal at or near the pK$_a$.

The metal ion-peptides of this invention may be used directly for administration, or alternatively may be conjugated to a carrier or targeting molecule. The methods for conjugating peptides to carrier molecules are well known to those skilled in the art. The conjugations may involve covalent binding through carbohydrate residues, sulfhydryl residues, amine groups (including those of lysine), and carboxyl groups.

The peptides of the invention can be:

a) naturally-occurring, b) produced by chemical synthesis, c) produced by recombinant DNA technology, d) produced by biochemical or enzymatic fragmentation of larger molecules, e) produced by methods resulting from a combination of a–d, or f) produced by any other means for producing peptides.

The peptides can also include peptide fragments, oliopeptides, polypeptides and other like structures, generally consisting of a sequence of amino acids. Representative types of peptides include those derived from laminin, fibronectin, cytokines, lymphokines, hormones, serum albumin, fibrinogen, enzymes, hormones, somatostatin, urokinase, tissue plasminogen activator, and protease inhibitors. The term "peptide" as used throughout the specification and claims is intended to include all of the foregoing.

The peptide of this invention is reacted with a medically useful metal ion. The medically useful metal ion may be radioactive and generate gamma rays, beta particles, or positrons which are converted into gamma rays upon collision with electrons. Alternatively, the medically useful metal ion may be paramagnetic. The medically useful metal ion may used in diagnostic imaging procedures including gamma scintigraphy, specific photon emission computerized tomography, or positron emission tomography. The medically useful metal ion may also be used diagnostically in magnetic resonance imaging. Medically useful metal ions may also be used therapeutically.

The type of medically useful metal ion depends on the specific medical application. Particularly useful metal ions can be found in the group consisting of elements 26–30 (Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Tl, Pb, Bi, Po, At). Isotopes of the elements Tc, Re, and Cu are particularly applicable for use in diagnostic imaging and radiotherapy. The isotope $^{99m}$Tc is particularly applicable for use in diagnostic imaging. Other radionuclides with diagnostic or therapeutic applications include $^{62}$Cu, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{211}$Pb and $^{212}$Bi.

The product resulting from the methods set forth herein can be used for both medical applications and veterinary applications. Typically, the product is used in humans, but may also be used in other mammals. The term "patient" is intended to denote a mammalian individual, and is so used throughout the specification and in the claims. The primary applications of the invention involve human patients, but the invention may be applied to laboratory, farm, zoo, wildlife, pet or sport animals.

The product may be used to monitor normal or abnormal metabolic events, to localize normal or abnormal tissues, to localize diseases, and to bind to blood constituents, including blood cells, such as lymphocytes, for subsequent localization of diseases, infections, and abnormal tissues. The application and medical use of the product depends on the type of peptide and the type of medically useful metal ion used.

Laminin peptide fragments, which bind to receptors found on platelets and on malignant cells, may be labeled with medically useful metal ions. Laminin peptide fragments have potential for use in thrombus imaging, through fragments binding to platelets, and for use in cancer diagnosis and therapy, through fragments binding to malignant cells. Laminin fragments are peptides which contain a biological-function domain consisting of Tyr-Ile-Gly-Ser-Arg (YIGSR).

Cells bind to laminin using several different types of cell surface receptors. One class of receptors is the integrins (Hynes RO: Integrins: a family of cell surface receptors. Cell 48:549, 1987) which bind adhesion molecules (laminin, fibronectin, thrombospondin, vitronectin, fibrinogen) containing the RGD sequence. At least four different integrins have been found to bind laminin, and two other receptors have been described. The 32,000 MW form found in mast cells binds a laminin peptide designated PA22-2 (CSRARKQAASIKVAVSADR) of which IKVAV is the active site (Thompson H. L., Burbelo P. D., Yamada Y., Kleinman H. K. and Metcalfe D. D.: Identification of an amino acid sequence in the laminin A chain mediating mast cell attachment and spreading, Immunol 72:144–149, 1991). The 67,000 MW receptor was originally found in tumor cells and binds YIGSR although other laminin domains may be involved. The isolated receptor retains a high affinity for laminin ($K_D$=2 nM) and has been reported in human breast carcinoma tissue, rodent striated muscle, murine fibrosarcoma, rodent macrophages, human monocytes, and murine melanoma cells.

Platelets have been found to have integrin type receptors (Sonnenberg A, Modermann PW and Horgervorst F: Laminin receptor on platelets is the integrin VLA-6, Nature 336:487–489, 1988), and are believed to bind laminin via the platelet glycoprotein Ic/IIa complex. Platelets also have a 67,000 MW receptor (Tandon N. N., Holland E. A., Kralisz U., Kleinman H. K., Robey F. A. and Jamieson G. A.: Interaction of human platelets with laminin and identification of the 67 kDa laminin receptor on platelets, Biochem J 274:535–542, 1991) for laminin. Platelet binding to laminin does not, in itself, result in platelet activation.

Malignant cells, when compared to normal counterparts, bind more readily to laminin, bind more total laminin, and support more laminin on their cell surfaces (Cioce V, Castronovo V., Shmookler B. M., Garbisa S., Grigioni W. F., Liotta L. A., and Sobel M. E.: Increased expression of the laminin receptor in human colon cancer, J Natl Cancer Inst 83:29–36, 1991). When added to metastatic cells laminin increases the invasive and metastatic activity of the cells and induces secretion of collagenase IV. These activities are related to binding to a high affinity (67,000 MW) receptor on the cell surface of the tumor cells. The binding of tumor cells to adhesion molecules, as well as their migration within extracellular matrices, plays an important role in the metastatic spread of malignant cancers. Laminin, its subunits, and synthetic peptides derived from it have been used for a number of years to inhibit experimental metastasis formation (Castronovo V., Taraboletti G. and Sobel M. E.: Laminin receptor complementary DNA-deduced synthetic peptide inhibits cancer cell attachment to endothelium, Cancer Res 51:5672–5678, 1991).

Other biologically active peptides include analogs of formyl peptide chemoattractants which bind to neutrophils. These peptides are based on the sequence N-formyl-Met-Leu-Phe.

The "C" terminal end can be modified to include additional sequences constituting a metal ion binding domain. The clinical and diagnostic imaging potential of formylated chemotactic peptides has recently been demonstrated by Fischman et al. (Fischman A. J., Pike M. C., Kroon D., Fucello A. J., Rexinger D., tenKate C., Wilkinson R., Rubin R. H. and Strauss H. W.: Imaging focal sites of bacterial infection in rats with indium-111-labeled chemotactic peptide analogs. *J Nucl Med* 32:483–491, 1991) using chemotactic peptides chemically conjugated to DTPA and subsequently labeled with $^{111}$In. Chemotactic peptides have also been radioiodinated by synthesizing formylated peptides containing tyrosine amino acids. These peptides have been used in vitro and have the same biological function as unlabeled formylated peptides (Janeczek A. H., Marasco W. A., Van Alten P. J. and Walter R. B.: Autoradiographic analysis of formylpeptide chemoattractant binding, uptake and intracellular processing by neutrophils. *J Cell Sci* 94:155–168, 1989).

Peptide analogues of somatostatin have been used after radiolabeling for diagnostic imaging. Somatostatin is a hormone produced by the hypothalamus which normally inhibits the release of pituitary growth hormone. A number of peptide analogues have been developed which have pharmacological actions that mimic the naturally-occurring hormone. Octreotide acetate, one of the somatostatin analogues, has a disulfide bond in it. In normal subjects somatostatin and its analogues have the ability to suppress secretion of serotonin and the gastroenteropancreatic peptides, and growth hormone. A number of tumor types have been found to express somatostatin receptors, with $^{125}$I-labeled somatostatin analogues used to image small-cell lung cancer (Kwekkeboom D. J., Krenning E. P., Bakker W. H. et al: Radioiodinated somatostatin analog scintigraphy in small-cell lung cancer. *J Nucl Med* 32:1845–1848, 1991).

The product can be used in a variety of medical procedures including gamma scintigraphy, specific photon emission computerized tomography, positron emission tomography, and magnetic resonance imaging. It is also possible to use the product to deliver a therapeutic quantity of radiation to a disease site. The medical application of the product of this invention depends on the type of peptide and the type of medically useful metal ion used.

In Rhodes B. A., U.S. Pat. No. 5,078,985, Radiolabeling Antibodies and Other Proteins with Technetium or Rhenium by Regulated Reduction, a process is taught in which disulfide bonds are first partially reduced with stannous salts or other disulfide reducing agents, the resulting combination is purified, and a specified amount of radionuclide reducing agent is added.

In Rhodes B. A., U.S. patent application Ser. No. 07/565,275, filed Aug. 8, 1990, entitled Direct Radiolabeling of Antibodies and Other Proteins with Technetium or Rhenium, a method, product and kit is provided, wherein proteins containing one or more disulfide bonds are radiolabeled with radionuclides for use in diagnosis and treatment of a variety of pathologic conditions. Radiolabeling is accomplished by partial reduction of the disulfide bonds of the protein using Sn (II), or using other reducing agents followed by the addition of Sn (II), removal of excess reducing agent and reduction by-products, and addition of a specified amount of radionuclide reducing agent, such as stannous tartrate, with the addition accomplished in such a manner that further reduction of the protein is limited. The methods and kit of the '275 application are useful in the present invention. The discussions therein pertaining to technetium and rhenium are also appropriate for the other radiometals and metal ionic forms described herein. Accordingly, the teachings of this application are incorporated herein by reference.

In Rhodes B. A. and Zamora P. O., U.S. patent application Ser. No. 07/816,477, entitled Direct Labeling of Antibodies and Other Proteins with Metal Ions, a method is taught in which a protein substrate, including peptides, containing monosulfides or disulfide bonds is labeled with a medically useful metal ion by the following method:

a) incubating the protein with a reducing agent to reduce some or all of the disulfide bonds to thiolate groups, or to maintain monosulfides as thiolate groups;

b) removing excess reducing agent from the protein substrate containing thiolate groups;

c) adding a source of Sn (II) agent to the thiolate-containing protein preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing protein form metal ion-containing and sulfur-containing complexes.

This invention also teaches that it is possible to chemically modify the protein by the introduction of disulfide bonds. A protein, even though it may not natively contain monosulfides or disulfide bonds, with attached or complexed disulfide bonds can be labeled. The discussions therein pertaining to medically useful metal ions are also appropriate for use with peptides described herein which contain cysteine or penicillamine, and thus contain one or more disulfide bonds or one or more monosulfides. Accordingly, the teachings of this application are incorporated herein by reference.

In Rhodes B. A., U.S. patent application Ser. No. 07/816,476, entitled Direct Radiolabeling of Antibody Against Stage Specific Embryonic Antigen for Diagnostic Imaging, antibody against stage specific embryonic antigen-1 is radiolabeled by direct means with a radionuclide for use in detection of occult abscess and inflammation. Radiolabeling is accomplished by partial reduction of the disulfide bonds of the antibody using Sn(II), or using other reducing agents followed by the addition of Sn(II), removal of excess reducing agent and reduction by-products, and addition of a specified amount of radionuclide reducing agent, such as stannous tartrate. The antibody is specific for human granulocytes, and can be used to image sites of occult abscess and inflammation. Accordingly, the teachings of this application are incorporated herein by reference.

In Rhodes B. A., a United States Patent Application filed concurrently herewith, entitled Leukostimulatory Agent for In Vivo Leukocyte Tagging, the use of a variety of leukostimulatory substances, including lectins, peptides and immunoglobulins, labeled or to be labeled with medically useful metal ions, is taught. These teachings, which also involve labeling through disulfide bonds or monosulfides, are specifically applicable to peptides containing cysteine or penicillamine. According, the teachings of that application are incorporated herein by reference.

There are two primary peptide configurations which require somewhat different methods in order to achieve stable labeling with a metal ion. One peptide configuration involves a metal ion-binding domain which includes one or more disulfide bonds. The most common example of this is $$(R_1)-[Cys-(R_2)-Cys]_n-(R_3),$$

wherein $[Cys-(R_2)-Cys]_n$ is the medically useful metal ion-binding domain, which can appear in the amino acid sequence from 1 time to about 6 times; and $R_1$, $R_2$ and $R_3$ are each amino acid sequences containing from 0 to about 20 amino acids, with at least one of the amino acid sequences $R_1$, $R_2$ and $R_3$ containing the biological-function domain. An example of a peptide fragment meeting this criteria is $$\ldots -Phe-Cys-Phe-Trp-Lys-Thr-Cys-Thr-\ldots$$

in which the biological-function domain is $R_2$, being the sequence Phe-Trp-Lys-Thr; the metal ion-binding domain is $[Cys-(R_2)-Cys]_n$, wherein n equals 1, being the sequence Cys-Phe-Trp-Lys-Thr-Cys; $R_1$ is the sequence . . . -Phe; and $R_3$ is the sequence Thr- . . . Other peptide configurations in which reducible disulfide bonds are present are also included in this method. These include the substitution of Pen for one or both Cys amino acids, as well as the modification of a native Met to allow it to form a disulfide bond. The biological-function domain can appear in any one of $R_1$, $R_2$ and $R_3$, and can also span more than one region, so that the biological-function domain may constitute, for example, $R_2$ and $R_3$, or some portion of $R_2$ and $R_3$. Any one or more of the regions $R_1$, $R_2$ and $R_3$ may contain no amino acids. Examples of peptides which contain disulfide bonds include antibiotic peptides such as defensin HNP-2, atrial natriuretic peptide and its analogues, diabetes-associated peptide, calcitonin, calcitonin gene related peptide, endothelin 1, endothelin 2, endothelin 3, $Pen^{2,5}$-enkephalin, transforming growth factor and related peptides, $[Cys^4, Phe^7, Cys^{10}]$ melanocyte stimulating hormone and its analogues, oxytocin and its analogues, vasopressin and its analogues, somatostatin and its analogues, and substance P analogues which contain cysteine-based disulfide bonds.

In those peptides in which the metal ion-binding domain includes one or more disulfide bonds, it is necessary to first reduce the disulfide bond or bonds. In a preferred embodiment, the following method is employed:

a) incubating the peptide with a reducing agent to reduce some or all of the disulfide bonds to thiolate groups;

b) removing excess reducing agent from the peptide substrate containing thiolate groups;

c) adding a source of Sn (II) agent to the thiolate-containing peptide preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing peptide form metal ion-containing and sulfur-containing complexes.

The order of the steps may be altered, and the method will still produce metal ion-labeled peptides. Accordingly, the claims are not limited to the order of steps presented therein. Specifically, it is possible, and in some cases advantageous, to add the Sn (II) to form Sn (II)-containing and sulfur-containing complexes prior to removing excess reducing agent from the peptide substrate. In this way, oxidation of thiolate groups or reformation of disulfide bonds and other cross-linkages is immediately minimized.

Numerous reducing agents have been described and are known to those skilled in the art. Particularly useful types of reducing agents include 2-mercaptoethanol; 1,4-dithiotheitol; 2,3-dihydroxybutane-1,4-dithiol; 2-aminoethanethiol HCl; 2-mercaptoethylamine; thioglycolate; cyanide; cysteine; reduced glutathione; Sn (II); Cu (I); and Ti (II). The reducing agent may be dissolved in a solute or may be attached to a solid phase. Reducing agents attached to a solid phase are commercially available, and methods for their use are known to those skilled in the art. The degree to which the peptide requires disulfide bond reduction depends on the nature of the peptide and its intended medical application. Generally speaking, milder reduction conditions and shorter incubation periods are required than is required to reduce disulfide bonds in proteins or complex polypeptides, such as antibodies. In any event, reduction is halted before excessive fragmentation of the peptide or loss of the biological-function of the peptide occurs.

In one specific embodiment, Sn (II) is used as a reducing agent at a concentration of 5 mM. In this embodiment the Sn (II) is dissolved in a buffer composed of approximately 10 mM tartrate and 40 mM phthalate, pH 5.5, and the Sn (II) buffer admixed with a peptide substrate at a concentration of 8.3 mg/ml. The reduction reaction is allowed to proceed for a period of time at room temperature, three hours having been employed successfully with some peptides containing a single disulfide bond, after which time the reaction is terminated by removing excess Sn (II) ions by molecular sieve chromatography. One means of molecular sieve chromatography employs Sephadex G-25, with the chromatography gel pre-equilibrated, and the peptide eluted in 0.9% NaCl or other suitable buffer.

Removal of the reducing agent, whether Sn (II) or some other reducing agent, can be accomplished by a variety of suitable means, including such methods as dialysis, ultrafiltration, positive-pressure membrane filtration, precipitation, preparative high performance liquid chromatography, affinity chromatography, other forms of chromatography and preparative isoelectric focusing. Many of the reducing agents contain thiols, which if present in the final labeling mixture, can complex with the medically useful metal ion. Such complexes can have severe and unknown side effects if administered in vivo. Additionally, some reducing agents exhibit unacceptable toxicity. Thus removal of the reducing agent both limits the degree of reduction to that desired, as well as providing for increased utility and safety of the labeled preparation by removal of toxic or otherwise undesirable reducing agents.

Thiolate groups in reduced peptides are highly reactive and can interact to reform disulfide bonds. The use of Sn (II) is believed to minimize the reformation of disulfide bonds. Sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mm. The stannous tartrate is added to the peptide after removal of the peptide-reducing agent. The stannous tartrate is prepared in a buffer composed of 10 mM tartrate and 40 mM phthalate, pH 5.6, and is added to peptide to yield a final concentration of 1 mg/ml peptide solution.

Sn (II) can be stabilized by use of dicarboxylic acids, such as phthalate and tartrate. A wide range of dicarboxylic acids, known to those skilled in the art, may be similarly used to stabilize the Sn (II) and/or to act as a buffer. If the phthalate and tartrate are in molar excess relative to the Sn (II), then these dicarboxylic acids also stabilize the medically useful metal ion in a form which can react with the peptide. In one embodiment tartrate and phthalate are used in the Sn (II) agent at concentrations of 10 mM and 40 mM, respectively.

Similarly, the Sn (II) and the medically useful metal ion may be stabilized by free amino acids used singly or in combination with other agents. The type of amino acid used and the specific concentration depends on the nature of the peptide and its intended use. In one embodiment, glycine is used at a concentration of 0.1–10 mM, and in another, histidine is used at a concentration of 0.1–10 mM.

The peptide may be stored frozen in bulk form after disulfide bond reduction and the removal of excess reducing agent. Alternatively, the peptide may be stored in bulk form or in unit dose form after addition of the Sn (II). Similarly, the peptide may be stored lyophilized during or after processing. For example, in one embodiment the peptide is stored in vials after introduction of the Sn (II). Methods used in lyophilization of peptides are known to those skilled in the art. Either frozen or lyophilized preparations may be maintained for an indefinite period before labeling by the addition of the medically useful metal ion.

In both the frozen and lyophilized storage forms, excipients may be added to the peptide to minimize damage which can arise from ice-crystal formation or free-radical formation. The type of excipient and the concentration depends on the nature of the peptide and the intended use. In one embodiment, glycine and inositol are used as excipients in lyophilized preparations.

A typical lyophilized preparation made by the embodiments set forth above would, upon rehydration, contain approximately 10 mM tartrate, 40 mM phthalate, 22 μg of Sn (II), 500 μg of peptide, 2 mg/ml of glycine, and 2 mg/ml of inositol. The amounts of peptide and Sn (II) used in the kits would depend on the medical application, varying depending on biodistribution of the peptide, imaging modality being used, type of metal ion and related factors. Similarly, the amount and type of buffer components (such as tartrate and phthalate) and excipients (such as glycine and inositol) depends on the specific application.

To label with a medically useful metal ion, a typical lyophilized preparation is hydrated by the addition of a solution containing 0.9% NaCl (U.S.P.) or water for injection (U.S.P.) and the medically useful metal ion. Alternatively, it is possible to hydrate the lyophilized preparation, and to add the metal ion in a subsequent step. If a frozen preparation is used, it is thawed and allowed to come to room temperature, and a solution containing the medically useful metal ion is then added. The nature and amount of the medically useful metal ion and the specific reaction conditions depend on the isotopic nature of the metal, and the intended medical application. In one embodiment, $^{99m}$Tc is added in the form of pertechnetate ion in a solution of 0.9% NaCl. The $^{99m}$Tc is typically incubated for up to 30 minutes to insure completion of the reaction with the peptide, after which the radiolabeled preparation can be directly used in medical applications. In another embodiment, $^{67}$Cu is added in a solution of 10 mM tartrate and 40 mM phthalate at pH 5.6. In yet another embodiment, $^{188}$Re or $^{186}$Re is added to a solution of 10 mM tartrate and 40 mM phthalate, at pH 5.6, and containing Sn (II), and then heated to lower the oxidation state of Re. The resulting solution is then added to the lyophilized or frozen preparation.

In the embodiment in which $^{99m}$Tc is used, the Sn (II) is present in the peptide-containing solution in sufficient excess to alter the oxidation state of the Tc ion such that it can bind to thiolate groups. Typically Tc (VII) is reduced to Tc (III), Tc (VI), and/or Tc (V). The preferred state of Tc to be added to peptide preparations is as the pertechnetate ion, (TcO$_4$)$^-$. The Sn (II) then reacts with the pertechnetate ion resulting in a lower oxidation state in which the Tc is reactive with thiolate groups. Similar approaches may be used to lower the oxidation state of other medically useful metal ions for subsequent binding to thiolate groups. The type of the metal ion, its isotopic nature, and concentration would depend on the intended medical application.

The other peptide configuration involves one or more amino acids containing sulfur, nitrogen or oxygen which is available for binding, or which can be made available for binding to metal ions. Commonly used amino acids include Cys, Pen and His, or any combination of them. This peptide configuration does not involve initial reduction of disulfide bonds. The simplest case takes the form $(R_1)-[Cys]_n-(R_2)$ wherein $[Cys]_n$ is the medically useful metal ion-binding domain and $n$ is typically a number between 1 and about 6; and $R_1$ and $R_2$ are each an amino acid sequence containing from 0 to about 20 amino acids, with at least $R_1$ and $R_2$ including the biological-function domain. In this and all related forms, it should be noted that $R_1$ and $R_2$ are interchangeable; either can contain the biological-function domain, the biological-function domain may include part or all of both $R_1$ and $R_2$, and the biological-function domain may constitute only a portion of the amino acid sequence in either $R_1$ or $R_2$. The order of components for these purposes can be varied, so that $(R_1)-[Cys]_n-(R_2)$, $(R_2)-[Cys]_n-(R_1)$, $[Cys]_n-(R_2)-(R_1)$, $[Cys]_n-(R_1)-(R_2)$ and the mirror images of the last two orderings are all equivalent, even though the resulting peptides may significantly differ in other aspects. A representative example of this form is the sequence Cys-Asp-Pro-Gly-Try-Ile-Gly-Ser-Arg in which the Cys is $[Cys]_n$ wherein $n$ is 1, Tyr-Ile-Gly-Ser-Arg is the biological-function domain $(R_1)$ and Asp-Pro-Gly is $(R_2)$, so that the structure of the sequence is $[Cys]_n-(R_2)-(R_1)$.

Other forms of the same general configuration include $(R_1)-[Cys-(R_2)-Cys]_n-(R_3)$, $(R_1)-[Cys-(R_2)-Pen]_n-(R_3)$, $(R_1)-[His-(R_2)-Cys]_n-(R_3)$, $(R_1)-[His-(R_2)-Pen]_n-(R_3)$, and $(R_1)-[His-(R_2)-His]_n-(R_3)$ wherein the sequence [ . . . ]$_n$ is the medically useful metal ion-binding domain with n typically being a number between 1 and about 6; and $R_1$, $R_2$ and $R_3$ are each an amino acid sequence containing from 0 to about 20 amino acids, with at least one of $R_1$, $R_2$ and $R_3$ including the biological-function domain. Here too the ordering is irrelevant to the functional description; for example, $(R_3)-[His-(R_2)-Cys]_n-(R_1)$, $(R_1)-(R_3)-[His-(R_2)-Cys]_n$, $(R_3)-(R_1)-[His-(R_2)-Cys]_n$, mirror images of the foregoing two orderings, all orderings in which the positions of His and Cys are reversed, and orderings in which the biological-function domain is present in the any of the three regions $R_1$, $R_2$ and $R_3$, any portion of the three regions $R_1$, $R_2$ and $R_3$, or any combination of the three regions $R_1$, $R_2$ and $R_3$, are all equivalent to the third configuration listed above, $(R_1)$-[His-$(R_2)$-Cys]$_n$-$(R_3)$. Each of the other foregoing configurations can be similarly described.

In one preferred embodiment of the method for labeling peptides of the configurations set forth above, the following method can be employed:

a) adding a source of positively-charged transition metal, most preferably an Sn (II) agent, to the peptide containing amino acids comprising sulfur, nitrogen or oxygen which is available for binding, or which can be made available for binding to metal ions, in an amount sufficient to allow the positively-charged transition metal to undergo a replacement reaction, thereby forming transition metal-containing and sulfur-, nitrogen- or oxygen-containing complexes, or some combination thereof; and, b) adding a medically useful metal ion whereby the metal ion displaces the transition metal in the transition metal-containing and sulfur-, nitrogen-or oxygen-containing complexes and the metal ion and peptide form metal ion-containing and sulfur-, nitrogen-, or oxygen-containing complexes.

The preferred transition metal is Sn (II); useful sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mM. The stannous tartrate is prepared in a buffer composed of 10 mM tartrate and 40 mM phthalate, pH 5.6, and is added to peptide to yield a final concentration of 1 mg/ml peptide solution.

As is the case in the method involving reduction of disulfide bonds, Sn (II) can be stabilized by use of dicarboxylic acids, such as phthalate and tartrate. A wide range of dicarboxylic acids, known to those skilled in the art, may be similarly used to stabilize the Sn (II) and/or to act as a buffer. If the phthalate and tartrate are in molar excess relative to the Sn (II), then these dicarboxylic acids also stabilize the medically useful metal ion in a form which can react with the peptide. In one embodiment tartrate and phthalate are used in the Sn (II) agent at concentrations of 10 mM and 40 mM, respectively.

Similarly, the Sn (II) and the medically useful metal ion may be stabilized by free amino acids used singly or in combination with other agents. The type of amino acid used and the specific concentration depends on the nature of the peptide and its intended use. In one embodiment, glycine is used at a concentration of 0.1-10 mM, and in another, histidine is used at a concentration of 0.1-10 mM.

The peptide may be stored in bulk form or in unit dose form after addition of the Sn (II) or other transition metal. For example, in one embodiment the peptide is stored at −20° C. in vials after introduction of the Sn (II). Methods used in lyophilization of peptides are known to those skilled in the art. Either frozen or lyophilized preparations may be maintained for an indefinite period before labeling by the addition of the medically useful metal ion.

In both the frozen and lyophilized storage forms, excipients may be added to the peptide to minimize damage which can arise from ice-crystal formation or free-radical formation. The type of excipient and the concentration depends on the nature of the peptide and the intended use. In one embodiment, glycine and inositol are used as excipients in lyophilized preparations.

A typical lyophilized preparation made by the embodiments set forth above would, upon rehydration, contain 10 mM tartrate, 40 mM phthalate, 22 µg of Sn (II), 500 µg of peptide, 2 mg/ml of glycine, and 2 mg/ml of inositol. To label with a medically useful metal ion, a typical lyophilized preparation is hydrated by the addition of a solution containing 0.9% NaCl (U.S.P.) or water for injection (U.S.P.) and the medically useful metal ion. Alternatively, it is possible to hydrate the lyophilized preparation, and to add the metal ion in a subsequent step. If a frozen preparation is used, it is thawed and allowed to come to room temperature, and a solution containing the medically useful metal ion is then added. The nature and amount of the medically useful metal ion and the specific reaction conditions depend on the isotopic nature of the metal, and the intended medical application. In one embodiment, $^{99m}$Tc is added in the form of pertechnetate ion in a solution of 0.9% NaCl. The $^{99m}$Tc is typically incubated for up to 30 minutes to insure completion of the reaction with the peptide, after which the radio-labeled preparation can be directly used in medical applications. In another embodiment, $^{67}$Cu is added in a solution of 10 mM tartrate and 40 mM phthalate at pH 5.6. In yet another embodiment, $^{188}$Re or $^{186}$Re is added to a solution of 10 mM tartrate and 40 mM phthalate, at pH 5.6, and containing Sn (II), and then heated to lower the oxidation state of Re. The resulting solution is then added to the lyophilized or frozen preparation.

In the embodiment in which $^{99m}$Tc is used, the Sn (II) is present in the peptide-containing solution in sufficient excess to alter the oxidation state of the Tc ion such that it can bind to ionizable groups. Similar approaches may be used to lower the oxidation state of other medically useful metal ions for subsequent binding to ionizable groups. The type of the metal ion, its isotopic nature, and concentration would depend on the intended medical application.

The invention is further illustrated by the following non-limiting examples.

EXAMPLE I

Cys-Asp-Pro-Gly-Try-Ile-Gly-Ser-Arg

The laminin nonapeptide is a synthesized peptide sequence derived from a biochemically-produced fragment of the larger laminin molecule. The biological-function domain is Tyr-Ile-Gly-Ser-Arg. The thiolate group of Cys is used to bind Tc. The peptide was dissolved directly in 10 mM tartrate/40 mM phthalate buffer, pH 5.6 (P/T buffer), to result in a solution containing 1.4 mg of peptide/ml. This solution was mixed (7:3) with P/T buffer containing 1.25 mM stannous tartrate. Aliquots of 0.5 ml was then dispensed into individual vials. Each kit contained 0.5 mg of peptide, 40 mM phthalate, 10 mM tartrate, and 22 µg of stannous tartrate. All solutions were purged with nitrogen prior to use and all preparations prepared under an anaerobic atmosphere. The peptides in the labeling kits were labeled with $^{99m}$Tc by addition of 1–2 mCi of sodium pertechnetate (U.S.P.) and allowing the reaction to proceed for 30 minutes.

The peptide is a cyclic octapeptide analogue of somatostatin. The biological-function portion of the molecule is associated with the Phe-Trp-Lys-Thr portion of the molecule. The disulfide bridge between the two cysteine residues is reduced using an Sn (II) reducing agent, presumptively forming sulfur-tin complexes. The peptide was obtained in acetate buffer pH 4.4. To the peptide containing solution was added (1:1) 10 mM tartrate/40 mM phthalate buffer, pH 5.6 (P/T buffer), to result in a solution containing 500 µg of peptide/ml. This solution was mixed (1:1) with P/T buffer containing 1.25 mM stannous tartrate, and allowed to incubate at room temperature for at least three hours. Aliquots of 0.5 ml were then dispensed into individual vials. Each kit contained 0.25 mg of peptide, 40 mM phthalate, 10 mM tartrate, and 44 µg of stannous tartrate. All solutions were purged with nitrogen prior to use and all preparations made under an anaerobic atmosphere. The peptide in the labeling kits was labeled with $^{99m}$Tc by addition of 1–2 mCi of sodium pertechnetate (U.S.P.) and allowing the reaction to proceed for 30 minutes.

EXAMPLE III

N-formyl-Met-Leu-Phe-Gly-His-Gly-Gly-His-Gly-His-Gly-Gly-His (derived from SEQ. ID NO. 6)

This peptide is a chemotactic peptide analogue, specifically an analogue of N-formyl-Met-Leu-Phe, one of several peptides which are chemotactic for cells of the lymphatic system. The sequence His-Gly-Gly-His-Gly-His-Gly-Gly-His is used to bind Tc. The peptide was dissolved directly in 10 mM tartrate/40 mM phthalate buffer, pH 5.6 (P/T buffer), to result in a solution containing 1.4 mg of peptide/ml. This solution was mixed (7:3) with P/T buffer containing 1.25 mM stannous tartrate. Aliquots of 0.5 ml was then dispensed into individual vials. Each kit contained 0.5 mg of peptide, 40 mM phthalate, 10 mM tartrate, and 22 µg of stannous tartrate. All solutions were purged with nitrogen prior to use and all preparations prepared under an anaerobic atmosphere. The peptides in the labeling kits were labeled with $^{99m}$Tc by addition of 1–2 mCi of sodium pertechnetate (U.S.P.) and allowing the reaction to proceed for 30 minutes.

EXAMPLE IV

To compare the potential binding of $^{99m}$Tc to histidine and cysteine, $^{99m}$Tc binding in three peptides with known amino acid sequences was evaluated. One peptide, with the amino acid sequence $H_2$N-Cys-Asp-Pro-Gly-Tyr-Ile-Gly-Ser-Arg, contained a single cysteine residue and no histidines, and was prepared and radiolabeled as set forth in Example I. Another peptide, with the sequence (Acetyl)-Asp-Arg-Val-Ile-His-Pro-Phe-His-Leu-Val-Ile-His-Asp, contained histidine residues but no cysteines or cystine, and was prepared and radiolabeled as set forth in Example III. The control, poly-tyrosine, contained neither histidine nor cysteine; it was prepared and radiolabeled as set forth in Example I.

The histidine-containing peptide bound some but not all the added $^{99m}$Tc. The cysteine-containing peptide bound essentially all of the added $^{99m}$Tc. Poly-tyrosine, the negative control material, did not label. These results were confirmed by conventional thin-layer chromatography.

EXAMPLE V

Laminin nonapeptide was prepared as set forth in Example I. The radiolabeling efficiency was found to be essentially 100% as determined by radio-HPLC, and verified by ILTC. When chromatographed by ITLC in 0.9% saline, the $^{99m}$Tc-laminin peptide remained near the origin while pertechnetate and reduced pertechnetate (presumably complexed to tartrate/phthalate) migrated to the solvent front. To evaluate colloid content, the $^{99m}$Tc-laminin peptide was chromatographed on ITLC strips coated with albumin using an ethanol/water/ammonia developing system. Less than 5% colloid was observed in the preparations. To further establish that colloid was not a significant factor, the $^{99m}$Tc-laminin peptide was chromatographed over Sephadex G-25 (PD-10 mini-columns) resulting in an elution profile with nearly all of the radioactivity eluted in or near the void volume.

The $^{99m}$Tc-laminin peptide was found to bind to human colon carcinoma cells of the cell line LS-174T, and to do so at a level higher than that of a corresponding negative control material, $^{99m}$Tc-human IgG (Table 1). Similarly, the $^{99m}$Tc-laminin peptide was found to bind to human platelets, also at a level higher than that of the corresponding negative control material, $^{99m}$Tc-human IgG (Table 2).

TABLE 1

BINDING OF $^{99m}$Tc-LAMININ NONAPEPTIDE AND $^{99m}$Tc-HUMAN IgG TO LS-174T COLON CARCINOMA CELLS

| Sample | Final Binding (CPM) | Percent of Control |
|---|---|---|
| EXPERIMENT ONE (n = 3) | | |
| $^{99m}$Tc-Human IgG (control) | 40,568 ± 11,275 | 100% |
| $^{99m}$c-Laminin | 98,194 ± 30,422 | 242% |
| EXPERIMENT TWO (n = 3), REPEAT OF EXPERIMENT ONE | | |
| $^{99m}$Tc-Human IgG (control) | 91,198 ± 41,545 | 100% |
| $^{99m}$Tc-Laminin | 276,977 ± 21,828 | 304% |

TABLE 2

BINDING OF $^{99m}$Tc-LAMININ NONAPEPTIDE AND $^{99m}$Tc-HUMAN IgG TO HUMAN PLATELETS AND CLOTS

| Sample | Final Binding (CPM) | Percent of Control |
|---|---|---|
| EXPERIMENT ONE (n = 3), PLATELETS IN PLATELET-RICH PLASMA | | |
| $^{99m}$Tc-Human IgG (control) | 76,986 ± 12,173 | 100% |
| $^{99m}$Tc-Laminin | 243,269 ± 43,838 | 315% |
| EXPERIMENT TWO (n = 3), CLOTS | | |
| $^{99m}$Tc-Human IgG (control) | 28,331 ± 7,233 | 100% |
| $^{99m}$Tc-Laminin | 159,763 ± 22,314 | 564% |

Clearance studies of the $^{99}$Tc-laminin peptide in normal rats revealed that the radioactivity was very rapidly cleared from the blood. The blood clearance was biphasic. The blood clearance was via the kidneys and to a lesser extent the hepatobiliary system. The biodistribution at 1.5 hours after injection did not reveal significant accumulations of the radiolabel in any organ examined other than the kidney.

EXAMPLE VI

Synthesis of Peptide Containing Biological-Function Domain and Metal Ion-Binding Domain The chemotactic peptide analogue N-formyl-Met-Leu-Phe-Gly-His-Gly-Gly-His-Gly-His-Gly-Gly-His was synthesized using a commercially available automated synthesizer. The peptide was lyophilized and purified using reverse phase HPLC. The peptide was then labeled using the methods of Example III.

In addition to the specific examples above, the methods of this invention have been successfully applied to the following peptides:

a) angiotensin I,
b) renin substrate tetradecapeptide,
c) hypercalcemia of malignancy factor fragment 1-16,
d) parathyroid hormone fragment 1-34,
e) poly(histidine-glutamic acid)-poly-alanine-poly-lysine, and
f) additional chemotactic peptide analogs.

All of the foregoing are merely illustrative, and other equivalent embodiments are possible and contemplated.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application, are hereby incorporated by reference.

---

What is claimed is:

1. A metal ion-labeled peptide complex comprising:
   a) a peptide including a biological-function domain and a metal ion-binding domain; and
   b) a metal ion complexed to the metal ion binding domain;
   wherein the metal ion-binding domain comprises one or more amino acids containing a sulfur atom which is available for binding to metal ions or which can be made available for binding to metal ions, and further includes one or more amino acids each containing at least one nitrogen atom or oxygen atom but not a sulfur atom which is available for binding to metal ions or which can be made available for binding to metal ions;
   wherein the biological-function domain is an amino acid sequence containing from 1 to about 20 amino acids; and
   wherein the peptide further comprises from 0 to about 20 amino acids not included within the metal ion-binding domain or the biological-function domain.

2. The complex of claim 1 wherein the metal ion-binding domain comprises one amino acid containing a sulfur atom which is available for binding to a metal ion or which can be made available for binding to a metal ion.

3. The complex of claim 1, wherein the metal ion-binding domain comprises two amino acids each containing a sulfur atom which is available for binding to a metal ion or which can be made available for binding to a metal ion.

4. The complex of claim 2 wherein said peptide has the formula:

$(R_1)-[Y_1-(R_2)-Y_2]-(R_3)$ wherein $Y_1$ and $Y_2$ are amino acids wherein either member of the pair consisting of $Y_1$ and $Y_2$ comprises a sulfur atom which is available for binding to a metal ion or can be made available for binding to a metal ion, and the other member of the pair consisting of $Y_1$ and $Y_2$ comprises at least one nitrogen atom or oxygen atom which is available for binding to a metal ion or which can be made available for binding to a metal ion; and
wherein the biological-function domain comprises at least a portion of one of the amino acid sequences $R_1$, $R_2$ and $R_3$, and wherein those of $R_1$, $R_2$ and $R_3$ or portions thereof not within the biological-function domain each comprise an amino acid sequence containing from 0 to about 20 amino acids.

5. The complex of claim 1, wherein the metal ion complexed to the metal ion binding domain is a positively-charged transition metal.

6. The complex of claim 5, wherein the positively-charged transition metal is stannous ion.

7. The complex of claim 1, wherein the metal ion complexed to the metal ion binding domain is a medically useful metal ion.

8. The complex of claim 7, wherein the medically useful metal ion is technetium or rhenium.

9. The complex of claim 7, wherein the medically useful metal ion is Tc-99m, Re-186 or Re-188.

10. A metal ion-labeled peptide complex comprising:
    a) a peptide including a biological-function domain and a metal ion-binding domain; and
    b) a metal ion complexed to the metal ion binding domain;
    wherein the metal ion-binding domain comprises two or more amino acids each containing at least one nitrogen atom but not a sulfur atom which is available for binding to a metal ion or which can be made available for binding to a metal ion;
    wherein the biological-function domain is an amino acid sequence containing from 1 to about 20 amino acids; and
    wherein the peptide further comprises from 0 to about 20 amino acids not included within the metal ion-binding domain or the biological-function domain.

11. The complex of claim 10, wherein the metal ion complexed to the metal ion binding domain is a positively-charged transition metal.

12. The complex of claim 11, wherein the positively-charged transition metal is stannous ion.

13. The complex of claim 10, wherein the metal ion complexed to the metal ion binding domain is a medically useful metal ion.

14. The complex of claim 13, wherein the medically useful metal ion is technetium or rhenium.

15. The complex of claim 13, wherein the medically useful metal ion is Tc-99m, Re-186 or Re-188.

* * * * *